United States Patent [19]

Christiansen et al.

[11] 4,331,663
[45] May 25, 1982

[54] 4α,5α-EPOXY-3,20-DIOXOPREGNANE-2α,16α-DICARBONITRILE AND INTERMEDIATES AND PROCESS FOR PREPARATION, METHOD OF USE AND COMPOSITIONS THEREOF

[75] Inventors: Robert G. Christiansen, Schodack; Malcolm R. Bell, East Greenbush; Harry P. Schane, Jr., Chatham, all of N.Y.

[73] Assignee: Sterling Drug Inc., New York, N.Y.

[21] Appl. No.: 275,294

[22] Filed: Jun. 19, 1981

[51] Int. Cl.³ .................... A61K 31/58; C07J 17/00
[52] U.S. Cl. ................... 424/241; 260/239.5; 260/397.3; 260/239.55 R
[58] Field of Search .................. 424/241; 260/239.5, 260/239.55

[56] References Cited

U.S. PATENT DOCUMENTS

| | | | |
|---|---|---|---|
| 3,135,743 | 6/1964 | Clinton et al. | 260/239.55 |
| 3,296,255 | 1/1967 | Clinton et al. | 260/239.55 |
| 3,960,842 | 6/1976 | Hoffer et al. | 260/397.1 |

OTHER PUBLICATIONS

Begue, Gustafsson and Goldman, Endocrinology, vol. 95, pp. 238-246, 1974.
Goldman and Sheth, Biochimica et Biophysica Acta, vol. 315, pp. 233-249, 1973.

*Primary Examiner*—Elbert L. Roberts
*Attorney, Agent, or Firm*—Theodore C. Miller; B. Woodrow Wyatt

[57] ABSTRACT

4α,5α-Epoxy-3,20-dioxopregnane-2α,16α-dicarbonitrile is prepared by decyclizing 4α,5α-epoxy-20-oxopregn-2-eno-[2,3−d]isoxazole-16α-carbonitrile with strong base and is useful as an inhibitor of mineralocorticoid production and/or action without concomitant glucocorticoid inhibition in primates.

10 Claims, No Drawings

4α,5α-EPOXY-3,20-DIOXOPREGNANE-2α,16α-DICARBONITRILE AND INTERMEDIATES AND PROCESS FOR PREPARATION, METHOD OF USE AND COMPOSITIONS THEREOF

BACKGROUND OF THE INVENTION

1. Field of the Invention

The invention relates to 4α,5α-epoxy-3,20-dioxopregnane-2α,16α-dicarbonitrile and intermediates and process for preparation, method of use and compositions thereof.

DESCRIPTION OF THE PRIOR ART

Clinton and Manson U.S. Pat. No. 3,296,255 broadly describes 2-cyano-3-oxo-steroids wherein the steroid moiety includes androstanes and pregnanes and, more particularly, androstanes and pregnanes substituted at the 16-position with, for example, "hydroxy, acyloxy, or oxo radicals . . . ; halogen atoms, preferably fluorine, chlorine or bromine . . . ; and lower-alkyl groups." 2-Cyano-3-oxo-steroids substituted at the 16-position by cyano specifically are neither described nor suggested. Example 21 describes 2α-cyano-4α,5α-epoxypregnane-3,20-dione, which has the structural formula

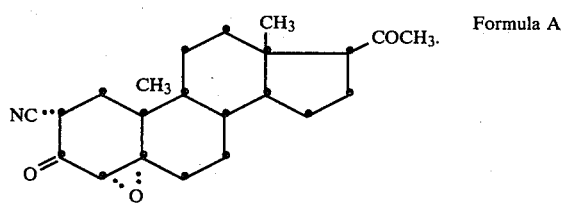

Formula A

The 2-cyano-3-oxo-steroids of the patent are disclosed as having "endocrinological and pharmacological activity, for example, adrenal inhibiting, pituitary inhibiting, electrolyte modifying, hypotensive and coronary dilator properties." No specific endocrinological properties of the compound of Formula A are disclosed. The 2-cyano-3-oxo steroids of the patent were prepared from the corresponding steroido-[2,3-d]isoxazoles, which are generically described by the parent patent, Clinton and Manson U.S. Pat. No. 3,135,743.

Begue, Gustafsson, and Goldman (Endocrinology, vol. 95, pp. 238–246, 1974) describe certain endocrinological properties of 2α,16α-dicyano-4,4'[sic]-dimethyl-5-pregnene-3,20-dione, which has the structural formula

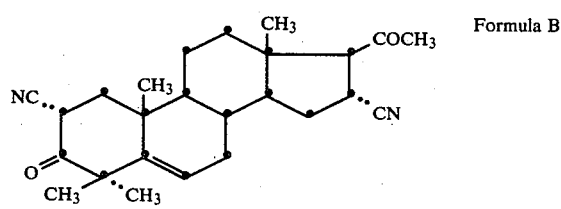

Formula B and which in vitro is an inhibitor of 3β-hydroxy-Δ⁵-steroid oxidoreductase and $C_{17-20}$ lyase and in vivo "alters adrenal and ovarian steroidogenesis with a concomitant excretion of 3β-hydroxy-Δ⁵-steroidal precursors." The effect of the compound of Formula B on human placental conversion of dehydroepiandrosterone and pregnenolone is described by Goldman and Sheth (Biochimica et Biophysica Acta, vol. 315, pp. 233–249, 1973). The compound is shown as Control No. 127 in Table VI at page 244. Control No. 128 in the same table is purportedly the 16α-cyano-20-keto[2,3-d]isoxazole derivative of Δ⁵-pregnene. Since the double bond at the 5-position in such a compound lacking substitution at the 4-position is unlikely, it seems likely that the compound of Control No. 128 was actually the corresponding 4,4-dimethyl compound and thus the isoxazole precursor of the compound of Control No. 127 and Formula B.

There is no compound of the prior art known to applicants which shows mineralocorticoid inhibition without concomitant glucocorticoid inhibition and without concomitant ovarian steroidogenesis inhibition in primates. Since diuretics undesirably induce hypokalemia as well as hypoaldosteronemia, such a compound would be useful in humans in treatment of these conditions with minimum risk of compensatory adrenal hypertrophy or inhibition of sex hormone production and is therefore an object of the invention.

SUMMARY OF THE INVENTION

In a composition of matter aspect the invention is 4α,5α-epoxy-3,20-dioxopregnane-2α,16α-dicarbonitrile having the structural formula

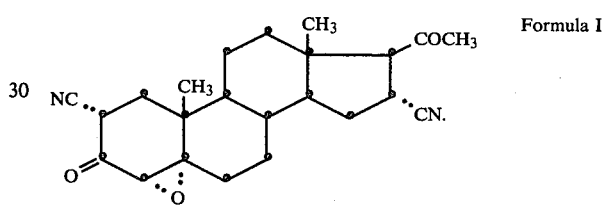

Formula I

The compound of Formula I is an inhibitor of mineralocorticoid production and/or action without concomitant glucocorticoid inhibition in primates and is therefore indicated for treatment of diuretic-induced hypokalemia and hyperaldosteronemia in humans.

In another composition of matter aspect the invention is 4α-5α-epoxy-20-oxopregn-2-eno[2,3-d]isoxazole-16α-carbonitrile having the structural formula

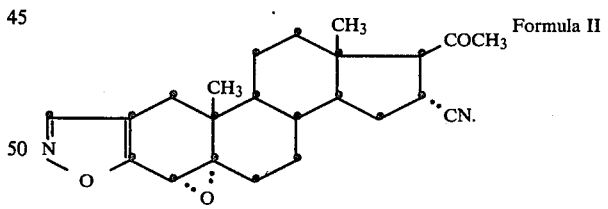

Formula II

In still another composition of matter aspect the invention is 20-oxopregna-2,4-dieno[2,3-d]isoxazole-16α-carbonitrile having the structural formula

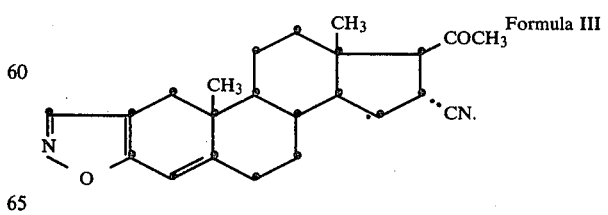

Formula III

In still another composition of matter aspect the invention is pregna-2,4,16-trieno[2,3-d]isoxazol-20-one having the structural formula

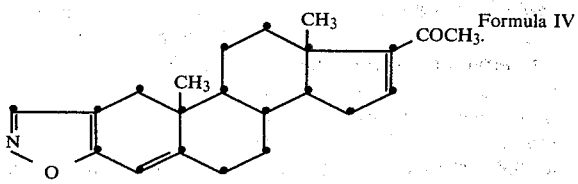

In still another composition of matter aspect the invention is pregna-2,4,16-trien-20-yno[2,3-d]isoxazole having the structural formula

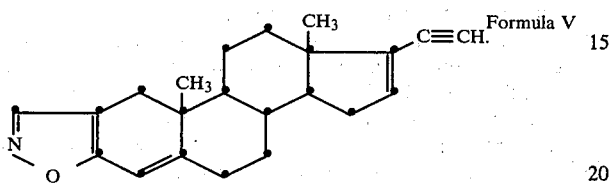

The compounds of Formulas II–V are useful as intermediates for preparing the compound of Formula I.

In a process aspect the invention is the process of preparing 4α,5α-epoxy-3,20-dioxopregnane-2α,16α-dicarbonitrile of Formula I which comprises the steps of (1) dehydrating pregna-2,4-dien-20-yno[2,3-d]isoxazol-17β-ol having the structural formula

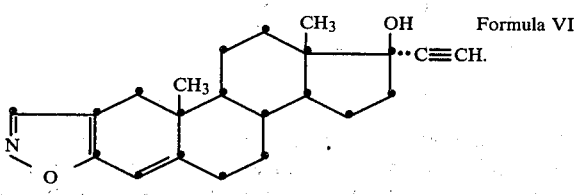

to form pregna-2,4,16-trien-20-yno[2,3-d]isoxazole of Formula V, (2) hydrating pregna-2,4,16-trien-20-yno[2,3-d]isoxazole of Formula V to form pregna-2,4,16-trieno[2,3-d]isoxazol-20-one of Formula IV, (3) hydrocyanating pregna-2,4,16-trieno[2,3-d]isoxazol-20-one of Formula IV to form 20-oxopregna-2,4-dieno[2,3-d]isoxazole-16α-carbonitrile of Formula III, (4) epoxidizing 20-oxopregna-2,4-dieno[2,3-d]isoxazole-16α-carbonitrile of Formula III to form 4α,5α-epoxy-20-oxopregn-2-eno[2,3-d]isoxazole-16α-carbonitrile of Formula II, and (5) decyclizing 4α,5α-epoxy-20-oxopregn-2-eno[2,3-d]isoxazole-16α-carbonitrile of Formula II with strong base to form 4α,5α-epoxy-3,20-dioxopregnane-2α,16α-dicarbonitrile of Formula I.

The process aspect of the invention is also the foregoing process step 5 done individually and the foregoing steps 2–5 done collectively.

In a method of use aspect the invention is the method of inhibiting mineralocorticoid production and/or action in a primate having an undesirably high plasma mineralocorticoid concentration which comprises administering to the primate an amount of 4α,5α-epoxy-3,20-dioxopregnane-2α,16α-dicarbonitrile of Formula I sufficient to reduce the plasma mineralocorticoid concentration.

In finally another composition of matter aspect the invention is a pharmaceutical composition for inhibiting mineralocorticoid production and/or action in a primate in solid or liquid dosage form for oral administration consisting essentially of 4α,5α-epoxy-3,20-dioxopregnane-2α,16α-dicarbonitrile of Formula I and a pharmaceutically acceptable vehicle.

DETAILED DESCRIPTION OF THE INVENTION INCLUSIVE OF THE PREFERRED EMBODIMENTS

Preparation of the Compounds

In the syntheses described below structures of products are inferred from known structures of starting materials and expected courses of preparative reactions and are confirmed by melting temperature range (m.r.), optical rotation ($[\alpha]_D^{25}$), elemental analysis, infrared spectral analysis, mass spectral analysis and/or thin-layer chromatography, which are also used to estimate purity of starting materials and products.

Pregna-2,4,16-trien-20-yno[2,3-d]isoxazole of Formula V

Preparation of the compound of Formula VI is described in Example 19 of above-cited Clinton and Manson U.S. Pat. No. 3,135,743.

Dehydration of the compound of Formula VI to form the compound of Formula V is accomplished using a phosphorus oxyhalide or a sulfur oxyhalide in the presence of a basic tertiary amine, for example, phosphoryl chloride in the presence of pyridine or 2,4-lutidine. The basic tertiary amine can serve as the solvent. Heating or cooling can be used to control the rate of reaction. With phosphoryl chloride in excess and 2,4-lutidine as solvent the dehydration is complete within a day at room temperature (15°–25° C.), but a higher or lower temperature within the range of 0°–100° C. can be used to increase or decrease the rate of reaction.

In an example, phosphoryl chloride (20.0 g.) was added with stirring to a mixture of pregna-2,4-dien-20-yno[2,3-d]isoxazol-17β-ol (20.0 g.) and 2,4-lutidine (120 ml.) and the resulting mixture was stirred overnight at room temperature, then quenched in ice-water containing concentrated hydrochloric acid (100 ml.). The resulting mixture was extracted twice with methylene dichloride. The combined methylene dichloride extracts were washed with water, dried over magnesium sulfate, filtered and stripped of solvent. Elution chromatography of the residue on silica gel (1 kg.) afforded in the pentane-ether-methylene dichloride (8:1:1) eluates a crystalline solid (11.74 g.), recrystallization of which from acetonitrile afforded pregna-2,4,16-trien-20-yno[2,3-d]isoxazole of Formula V (10.20 g., m.r. 163°–167° C., $[\alpha]_D^{25} + 175.0°$).

Pregna-2,4,16-trieno[2,3-d]isoxazol-20-one of Formula IV

Hydration of the compound of Formula V to form the compound of Formula IV is accomplished with formic acid with or without a mercuric salt as catalyst or with a mercuric salt in the presence of a sulfonated polystyrene resin. In the former method 90% formic acid has been successfully used with or without a cosolvent, for example, dimethylformamide. In the latter method an aqueous-alcoholic solvent, for example aqueous methanol, is used. Mercuric acetate has been successfully used as the mercuric salt catalyst in both methods. Heating or cooling can be used to control the rate of reaction. Heating is generally required, for example at steam bath temperature, with 90% formic acid. Room temperature is sufficient with 90% formic acid-mercuric acetate. With aqueous methanol-mercuric acetate the hydration is carried out at the reflux temperature of the mixture.

In an example, a mixture of pregna-2,4,16-trien-20-yno[2,3-d]isoxazole (2.10 g.) and 90% formic acid (50 ml.) was heated for two hours on a steam bath, then stripped of solvent under reduced pressure. The procedure was repeated using 7.98 g. of pregna-2,4,16-trien-20-yno[2,3-d]isoxazole and 200 ml. of 90% formic acid. Elution chromatography of the combined crude products on silica gel (500 g.) afforded in the pentane-ether-methylene dichloride (7:2:1) eluates a crystalline solid (5.60 g.), recrystallization of which from ethyl acetate afforded pregna-2,4,16-trieno[2,3-d]isoxazol-20-one of Formula IV (5.40 g., m.r. 176°–178° C., $[\alpha]_D^{25}+200.6°$).

20-Oxopregna-2,4-dieno[2,3-d]isoxazole-16α-carbonitrile of Formula III

Hydrocyanation of pregna-2,4,16-trieno[2,3-d]isoxazol-20-one of Formula IV to form 20-oxopregna-2,4-dieno[2,3-d]isoxazole-16α-carbonitrile of Formula III is accomplished using a trialkylaluminum and hydrogen cyanide or a dialkylaluminum cyanide, especially diethylaluminum cyanide, in an inert, non-polar solvent, for example, benzene, toluene or ether or a combination thereof. Heating or cooling can be used to control the rate of reaction. With diethylaluminum cyanide the reaction is preferably carried out at ice-water temperature under a nitrogen atmosphere.

In an example, a solution of diethylaluminum cyanide in toluene (2 M, 175 ml.) was added slowly with stirring to a solution of pregna-2,4,16-trieno[2,3-d]isoxazole-20-one (54.36 g.) in benzene (1000 ml.), which was prepared with warming, filtering the slightly turbid solution through silica gel (50 g.) and rinsing the silica gel with a small amount of dry ether and which was maintained at ice-water temperature under a nitrogen atmosphere during the addition. Stirring was continued for two hours, then saturated aqueous ammonium chloride solution was slowly added. Hydrogen cyanide was released with a surge and the reaction mixture was spattered around the hood. This can be avoided by first slowly adding alcohol (95%), then cautiously adding the saturated aqueous ammonium chloride solution with vigorous stirring. Most of the product was nevertheless recovered from what remained in the reaction flask and what could be scraped from the hood. Crystallization of the product thus obtained from aqueous ethanol and recrystallization first from ethanol and then from acetonitrile afforded 20-oxopregna-2,4-dieno[2,3-d]isoxazole-16α-carbonitrile of Formula III (12.65 g., m.r. 194°–196° C., $[\alpha]_D^{25}+161.5°$).

4α,5α-Epoxy-20-oxopregn-2-eno[2,3-d]isoxazole-16α-carbonitrile of Formula II

Epoxidation of 20-oxopregna-2,4-dieno[2,3-d]isoxazole-16α-carbonitrile of Formula III to form 4α,5α-epoxy-20-oxopregn-2-eno[2,3-d]isoxazole-16α-carbonitrile of Formula II is accomplished using a percarboxylic acid, for example m-chloroperbenzoic acid, in an inert, non-polar solvent, for example, methylene dichloride. Heating or cooling can be used to control the rate of reaction. With m-chloroperbenzoic acid and methylene dichloride the reaction is preferably carried out at ice-water temperature.

In an example, m-chloroperbenzoic acid (23 g.) was added to a solution of 20-oxopregna-2,4-dieno[2,3-d]isoxazole-16α-carbonitrile (35 g., residual resin from mother liquors of crystallization of 58.40 g. of the compound of Formula III obtained from a hydrocyanation of 83 g. of the compound of Formula IV) in methylene dichloride (500 ml.) with stirring at ice-water temperature, and stirring was continued for four hours. Aqueous sodium sulfite solution in excess of that required to destroy the excess peracid was added, followed by sodium bicarbonate in small portions. The organic layer was washed with aqueous sodium bicarbonate solution, dried over potassium carbonate, filtered, partially stripped of solvent and refiltered to remove unwanted crystals (0.67 g.). The crystals were washed with ethyl acetate and the filtrate was concentrated. The product crystallized from the concentrated filtrate in three crops (5.50 g., 3.90 g., 3.17 g, all having m.r. 226°–229° C.), which were combined and recrystallized from methylene dichloride-ethanol, affording, again in three crops which were combined, 4α,5α-epoxy-20-oxopregn-2-eno[2,3-d]-isoxazole-16α-carbonitrile of Formula II (10.42 g., m.r. 232°–235° C., $[\alpha]_D^{25}+143.4°$).

4α,5α-Epoxy-3,20-dioxopregnane-2α,16α-dicarbonitrile of Formula I

Decyclization of 4α,5α-epoxy-20-oxopregn-2-eno[2,3-d]isoxazole-16α-carbonitrile of Formula II to form 4α,5α-epoxy-3,20-dioxopregnane-2α,16α-dicarbonitrile of Formula I is accomplished as described by above-cited Clinton and Manson U.S. Pat. No. 3,296,255, that is, with a strong base, preferably an alkali metal hydroxide or alkoxide, for example potassium hydroxide or sodium methoxide, in an anhydrous medium, for example methanol or tetrahydrofuran, or a mixture thereof. Heating or cooling can be used to control the rate of reaction. With potassium hydroxide and a mixture of methanol and tetrahydrofuran the reaction is preferably carried out at room temperature.

In an example, a mixture of 4α,5α-epoxy-20-oxopregn-2-eno[2,3-d]isoxazole-16α-carbonitrile (44.0 g.), potassium hydroxide (15 g.), methanol (1000 ml.) and tetrahydrofuran (500 ml.) was stirred for about two hours at room temperature. Water (500 ml.) was added, the resulting mixture was allowed to stand overnight, more water (2 l.) was added, and the resulting solution was extracted with ether. The ethereal extract gave very little residue upon evaporation of the ether. The aqueous layer was slowly acidified with dilute aqueous sulfuric acid. A white solid (21.8 g.) slowly precipitated. Recrystallization of the solid from acetone-ethyl acetate afforded 4α,5α-epoxy-3,20-dioxopregnane-2α,16α-carbonitrile of Formula I (23.80 g., m.r. 228°–234° C., $[\alpha]_D^{25}+55.2°$).

BIOLOGICAL PROPERTIES OF COMPOUND OF FORMULA I AND COMPARISON WITH THOSE OF PRIOR ART COMPOUND OF FORMULA A

As stated above the compound of Formula I is an inhibitor of mineralocorticoid production and/or action without concomitant glucocorticoid inhibition in primates. This utility has been shown in the monkey as a test primate.

The compound of Formula I was tested preliminarily in the rat and was compared with the prior art compound of Formula A in the same tests in both the rat and the monkey. In the rat both compounds prevented furosemide-induced kaliuresis without causing adrenal hypertrophy. In the monkey the compound of Formula A had no effect on furosemide-induced hyperaldosteronemia or ACTH-induced cortisol production, whereas the compound of Formula I inhibited furosemide-induced hyperaldosteronemia without inhibiting ACTH-induced cortisol production.

To test for furosemide-induced kaliuresis in the rat, groups of eight mature male rats each weighing about 200 g. were fasted overnight, then injected intraperitoneally with Krebs' Ringer phosphate solution (5 ml./100 g.) and placed in metabolism cages. Urine from each rat was collected for five hours. Furosemide (25 mg. 1 kg.) formulated in an aqueous sodium chloride (0.9%)-methylcellulose (0.75%) vehicle was administered orally three times, once at the beginning and again at two and four hours after the beginning of the collection period. The test compound (50 mg./kg.) formulated in the same vehicle was also administered orally three times, once two hours before, once at the beginning, and once two hours after the beginning of the collection period. Urine volumes and amounts of excreted sodium and potassium were measured for each rat and averaged for each group. Tests were also made of vehicle alone without furosemide and test compound and furosemide and vehicle alone without test compound. The results summarized in Table I show that both the compound of Formula I and the compound of Formula A prevented furosemide-induced kaliuresis in this test. The compound of Formula I differed from the compound of Formula A in also causing a modest but significant decrease in urine output.

dose of 200 mg./kg. Daily smears were read for vaginal estrus and feed consumption was measured. One day after the last medication the rats were weighed and killed, and selected organs were excised and weighed. Rats medicated with the vehicle alone served as controls. The results summarized in Table II show that the compound of Formula I did not significantly change any measured parameter and that the compound of Formula A caused a significant ($p<0.01$) but slight (20%) increase in adrenal weights, which is considered unimportant, but did not significantly change any other measured parameter.

TABLE II

| | Test of Endocrine Balance in Mature Female Rats | | | |
|---|---|---|---|---|
| | Test 1 | | Test 2 | |
| Weight | Vehicle | Compound of Formula I | Vehicle | Compound of Formula A |
| Initial Body (g.) | | | 198 ± 1.1 | 198 ± 1.6 |
| Final Body (g.) | | | 241 ± 1.9 | 239 ± 5.6 |
| Body Gain (g./day) | 2.6 ± 0.3 | 2.9 ± 0.3 | | |
| Food Consumed (g./day) | 17.7 ± 0.5 | 18.0 ± 0.4 | 16.4 ± 0.5 | 15.8 ± 0.4 |
| Thymus (mg.) | 397.8 ± 34.7 | 403.9 ± 32.8 | 466.6 ± 31.5 | 410.8 ± 31.8 |
| Adrenals (mg.) | 68.3 ± 3.4 | 80.4 ± 3.4 | 66.5 ± 3.2 | 80.0 ± 2.9 |
| Uterus (mg.) | 354.2 ± 28.4 | 373.0 ± 35.0 | 394.1 ± 29.9 | 379.1 ± 41.3 |
| Ovary (mg.) | 83.9 ± 4.5 | 88.3 ± 4.5 | 86.7 ± 3.7 | 97.8 ± 2.3 |
| Percent Vaginal Estrous Days | 27% | 27% | 24% | 23% |

To test for effects on furosemide-induced hyperaldosteronemia and ACTH-induced cortisol production in the monkey, groups of monkeys were fasted overnight and the following morning was simultaneously medicated orally with furosemide (100 mg./monkey), subcutaneously with ACTH (40 IU/monkey of Armour ACTHAR Gel of 80 IU/ml.), and orally with the test compound formulated in an aqueous gum tragacanth (1%) vehicle (100 ml./monkey). Monkeys medicated with the gum tragacanth vehicle alone served as controls. Four hours later a blood sample was taken from each monkey, and the heparinized plasma from each sample was assayed for aldosterone and cortisol concentrations by radioimmunoassay. The results summarized in Table III show that the compound of Formula I inhibited aldosterone production but had no effect on circulating cortisol levels at a dose of 10 mg./monkey (about 1.5 mg./kg.) and inhibited aldosteone production but did not lower cortisol levels even at a dose of 500 mg./monkey (about 75 mg./kg.), whereas the compound of Formula A had no effect on either aldosterone production or circulating cortisol levels at a dose of 500 mg./monkey.

TABLE I

| | | Test of Furosemide-Induced Kaliuresis in Rats | | | |
|---|---|---|---|---|---|
| | | Urinary Excretion Parameters | | | |
| Test | Medication[a] | Volume(ml.) | Sodium(meq.) | Potassium(meq.) | Na/K Ratio |
| 1 | V | 3.6 ± 0.4 | 0.90 ± 0.08 | 0.18 ± 0.02 | 5.4 ± 0.5 |
| 2 | V | 5.5 ± 0.8 | 1.33 ± 0.13 | 0.32 ± 0.02 | 4.2 ± 0.2 |
| 3 | V | 4.1 ± 0.5 | 0.88 ± 0.09 | 0.21 ± 0.03 | 4.38 ± 0.41 |
| 1 | V + F | 17.4 ± 0.6 | 2.50 ± 0.07 | 0.54 ± 0.02 | 4.7 ± 0.2 |
| 2 | V + F | 19.8 ± 0.8 | 2.95 ± 0.11 | 0.63 ± 0.04 | 4.7 ± 0.2 |
| 3 | V + F | 17.1 ± 1.1 | 2.69 ± 0.14 | 0.55 ± 0.04 | 5.13 ± 0.48 |
| 1 | V + F + I | 12.3 ± 1.3[b] | 2.04 ± 0.18 | 0.27 ± 0.02[c] | 7.7 ± 0.5[c] |
| 2 | V + F + I | 12.4 ± 0.8[c] | 2.29 ± 0.16 | 0.27 ± 0.01[c] | 8.6 ± 0.2[c] |
| 3 | V + F + A | 16.3 ± 1.5 | 2.74 ± 0.2 | 0.38 ± 0.03[c] | 8.39 ± 0.67 |

[a] V = vehicle F = Furosemide I = compound of Formula I A = compound of Formula A
[b] Differs from V + F group, $p < 0.01$
[c] Differs from V + F group, $p < 0.001$ To test for adrenal hypertrophy and other endocrine changes in the rat, groups of eight mature female rats each weighing about 200 g. were medicated with the test compound formulated in an aqueous gum tragacanth (1%) vehicle orally for 14 consecutive days at a

TABLE III

Test of Effects on Aldosterone and Cortisol Levels in Monkeys

| Test | Medication | Dose (mg./monkey) | Cortisol (μg./100ml.) | Aldosterone (ng./100ml.) |
|---|---|---|---|---|
| 1 | Vehicle | | 63 (47–82)[a] | 84 (47–142)[a] |
| 1 | Compound of Formula I | 10 | 54 (41–65)[a] | 47 (27–75)[a,b] |
| 2 | Vehicle | | 67 (55–85)[a] | 76 (54–95)[a] |
| 2 | Compound of Formula I | 500 | 51 (41–72)[a] | 33 (23–45)[a,b] |
| 3 | Vehicle | | 63 (48–71)[c] | 43 (35–53)[d] |
| 3 | Compound of Formula A | 500 | 43 (37–61)[c] | 41 (39–71)[c] |

[a]Fifteen monkeys
[b]Differs from median of control group at the 99% confidence level
[c]Five monkeys
[d]Four monkeys

THE COMPOSITIONS

Oral administration of the compound of Formula I is preferred over the other possible routes of administration. For this route of administration the appropriate conventional pharmaceutical vehicles and adjuncts can be used to prepare liquid and solid dosage forms as solutions, supensions, emulsions, capsules and tablets. The preferred dosage form is tablet or capsule.

We claim:

1. 4α,5α-Epoxy-3,20-dioxopregnane-2α,16α-dicarbonitrile having the structural formula

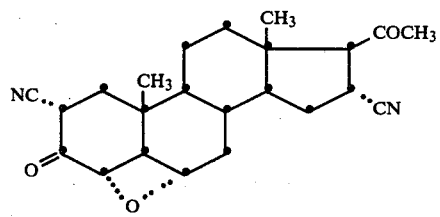

2. 4α,5α-Epoxy-20-oxopregn-2-eno[2,3-d]isoxazole-16α-carbonitrile having the structural formula

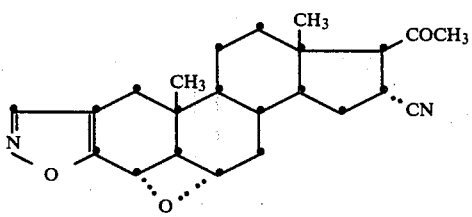

3. 20-Oxopregna-2,4-dieno[2,3-d]isoxazole-16α-carbonitrile having the structural formula

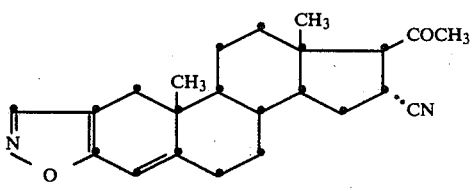

4. Pregna-2,4,16-trieno[2,3-d]isoxazol-20-one having the structural formula

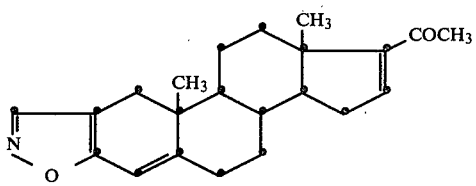

5. Pregna-2,4,16-trien-20-yno[2,3-d]isoxazole having the structural formula

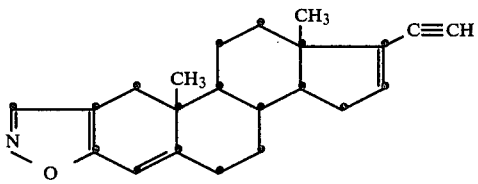

6. The process of preparing 4α,5α-epoxy-3,20-dioxopregnane-2α,16α-dicarbonitrile which comprises the step of decyclizing 4α,5α-epoxy-20-oxopregn-2-eno[2,3-d]isoxazole-16α-carbonitrile with strong base.

7. The process according to claim 6 which comprises the three prior steps of (a) hydrating pregna-2,4,16-trien-20-yno[2,3-d]isoxazole to form pregna-2,4,16-trieno[2,3-d]isoxazol-20-one, (b) hydrocyanating pregna-2,4,16-trieno[2,3-d]isoxazol-20-one to form 20-oxopregna-2,4-dieno[2,3-d]isoxazole-16α-carbonitrile, and (c) epoxidizing 20-oxopregna-2,4-dieno[2,3-d]isoxazole-16α-carbonitrile to form 4α,5α-epoxy-20-oxopregn-2-eno[2,3-d]isoxazole-16α-carbonitrile.

8. The process according to claim 7 which comprises the prior step of dehydrating pregna-2,4-dien-20-yno[2,3-d]isoxazole-17β-ol to form pregna-2,4,16-trien-20-yno[2,3-d]isoxazole.

9. The method of inhibiting mineralocorticoid production and/or action in a primate having an undesirably high plasma mineralocorticoid concentration which comprises administering to the primate an amount of 4α,5α-epoxy-3,20-dioxopregnane-2α,16α-dicarbonitrile sufficient to reduce the plasma mineralocorticoid concentration.

10. A pharmaceutical composition for inhibiting mineralocorticoid production and/or action in a primate in solid or liquid dosage form for oral administration consisting essentially of 4α,5α-epoxy-3,20-dioxopregnane-2α,16α-dicarbonitrile and a pharmaceutically acceptable vehicle.

* * * * *